US010463321B2

(12) United States Patent
Dekel et al.

(10) Patent No.: US 10,463,321 B2
(45) Date of Patent: Nov. 5, 2019

(54) APPLIANCE FOR DENTAL NAVIGATION

(71) Applicant: Claronav Inc., North York (CA)

(72) Inventors: Doron Dekel, Toronto (CA); Arish Qazi, Oakville (CA); Ido Bermanis, Vaughan (CA)

(73) Assignee: CLARONAV INC., North York (CA)

( * ) Notice: Subject to any disclaimer, the term of this patent is extended or adjusted under 35 U.S.C. 154(b) by 176 days.

(21) Appl. No.: 15/527,087

(22) PCT Filed: Dec. 8, 2015

(86) PCT No.: PCT/CA2015/051287
§ 371 (c)(1),
(2) Date: May 16, 2017

(87) PCT Pub. No.: WO2016/090476
PCT Pub. Date: Jun. 16, 2016

(65) Prior Publication Data
US 2018/0279975 A1    Oct. 4, 2018

Related U.S. Application Data

(60) Provisional application No. 62/088,787, filed on Dec. 8, 2014.

(51) Int. Cl.
*A61B 6/14* (2006.01)
*A61B 6/03* (2006.01)
(Continued)

(52) U.S. Cl.
CPC ............... *A61B 6/14* (2013.01); *A61B 6/03* (2013.01); *A61B 6/032* (2013.01); *A61C 9/004* (2013.01);
(Continued)

(58) Field of Classification Search
CPC .. A61B 6/14; A61B 6/032; A61B 6/03; A61B 2090/3966; A61B 2021/005; A61C 9/004; A61C 19/045
(Continued)

(56) References Cited

U.S. PATENT DOCUMENTS 8,348,669 B1 * 1/2013 Schmitt ............... A61C 9/0046
433/213
2013/0085721 A1 * 4/2013 Chishti ................. A61C 7/002
703/1

FOREIGN PATENT DOCUMENTS

WO        2012068679         5/2012
WO    WO-2012068679 A1 *  5/2012  ............... A61B 6/12

OTHER PUBLICATIONS

Written Opinion of the International Searching Authority and International Search Report for PCT/CA2015/051287 dated Apr. 12, 2016.

* cited by examiner

*Primary Examiner* — Matthew M Nelson
(74) *Attorney, Agent, or Firm* — Bereskin & Parr LLP/S.E.N.C.R.L., s.r.l.

(57) ABSTRACT

An apparatus, method and kit are provided for registering a human jaw with a CT image of the human jaw. The apparatus includes a moldable retainer and an arm having a moldable link portion and a rigid fixation portion. The link portion is attachable to the retainer and hardenable to maintain a fixed mapping between the fixation portion and the retainer. The fixation portion includes a CT marker connection region for detachably attaching a CT marker that includes a fiducial. The fixation portion also includes a tag connection region for detachably attaching a tag that is trackable by a pose measurement system. The pose of the tag connection region relative to a pose of the CT marker connection region is fixed prior to attaching either the tag or the CT marker, providing a known and fixed tag to fiducial coordinate mapping.

6 Claims, 14 Drawing Sheets

(51) Int. Cl.
*A61C 19/045* (2006.01)
*A61C 9/00* (2006.01)
*A61B 90/00* (2016.01)

(52) U.S. Cl.
CPC .... *A61C 19/045* (2013.01); *A61B 2090/3966* (2016.02); *A61C 2201/005* (2013.01)

(58) Field of Classification Search
USPC .......................................................... 433/68
See application file for complete search history.

APPLIANCE FOR DENTAL NAVIGATION

RELATED APPLICATIONS

This application is a National Stage of co-pending International Application No. PCT/CA2015/051287 filed Dec. 8, 2015, which claims the benefit of Provisional Application No. 62/088,787, filed Dec. 8, 2014, the contents of both of which are herein incorporated in their entirety by reference.

FIELD

The described embodiments relate to the field of medicine, in particular, the field of dental navigation systems.

BACKGROUND

PCT Application No. PCT/CA2011/001294, incorporated herein by reference in its entirety, teaches the use of an apparatus conforming to the surface of an anatomical region to attach one or more rigid bodies to the anatomical region at a repeatable position relative to the anatomical region. Such repeatable fixation may enable geometrical mapping of anatomical regions across clinical procedures performed at different times. For example, during a surgical procedure, an anatomical region may be dynamically registered with an image of the anatomical region to provide guidance to the surgeon. As well, the range and patterns of motions of anatomical regions may be measured and compared. Furthermore, the anatomical region may be repositioned relative to an instrument for various forms of treatment.

PCT Application No. PCT/CA2015/050025, incorporated herein by reference in its entirety, teaches a moldable appliance containing a rigid fiducial body that includes a plurality of feature regions and that defines a fiducial plane. PCT Application No. PCT/CA2015/050025 describes a fiducial body embedded in the moldable portion, and having the complete appliance, including the fiducial body, molded and attached to the jaw both during scanning and during surgery.

Prior designs may have a number of important drawbacks. For example, it can be difficult to mold the appliance directly in the patient's mouth, in particular for the lower jaw, because the patient's lips may apply a substantial force pushing the appliance off the jaw. Users may also find it difficult to hold the jaw-facing surface tight against the teeth while the appliance is hardening. Similarly challenges may arise during surgery, where the force of the patient's lips may lift the appliance off its seating on the teeth. Furthermore, some prior designs include fiducial bodies having exposed sharp corners that may cause discomfort and pain to patients during fabrication.

SUMMARY

In accordance with an embodiment, there is provided an apparatus for registering a human jaw with a volumetric CT (computerized X-ray tomography) image of the human jaw. The apparatus may include a retainer appliance configured to be moldable to an appliance geometry that mates with a surface geometry of at least a portion of the human jaw, such that when mated with the human jaw, the retainer appliance resists displacement relative to the human jaw, the retainer appliance being further configured to be hardenable to remain rigid and resist deformation once molded to the appliance geometry, and an arm comprising a moldable link portion and a rigid fixation portion. The link portion can be rigidly attachable to the retainer appliance and hardenable to remain rigid and resist deformation once hardened to maintain a fixed spatial mapping between the fixation portion and the retainer appliance when the link portion is rigidly attached to the retainer appliance. The fixation portion can include CT marker engaging surfaces for i) indicating a CT marker connection region, ii) aligning the CT marker connection region with corresponding surfaces of a CT marker, the CT marker including a fiducial detectable in the volumetric CT image, the fiducial shaped to allow a pose of the CT marker to be uniquely determinable in the volumetric CT image, and iii) contacting the corresponding surfaces of the CT marker at the CT marker connection region such that when the arm is detachably attached to the CT marker with the CT marker engaging surfaces in contact with the corresponding surfaces of the CT marker at the CT marker connection region the CT marker is maintainable in a fixed CT marker spatial relationship with the arm, and a pose of the fixation portion is thereby determinable from the pose of the CT marker. The fixation portion can also include tag engaging surfaces for i) indicating a tag connection region, ii) aligning the tag connection region with corresponding surfaces of a tag, the tag being measurable by a pose measurement system to determine a pose of the tag in a reference coordinate space, and iii) contacting the corresponding surfaces of the tag at the tag connection region such that when the arm is detachably attached to the tag with the tag engaging surfaces in contact with the corresponding surfaces of the tag at the tag connection region the tag is maintainable in a fixed tag spatial relationship with the arm. A pose of the tag connection region relative to a pose of the CT marker connection region can be fixed prior to attaching any one of the tag and the CT marker.

In some embodiments, the CT marker engaging surfaces can include a first CT marker connector having a CT marker connector geometry configured to detachably mate with a second CT marker connector geometry of a second CT marker connector provided by the corresponding surfaces of the CT marker such that, when the first CT marker connector and the second CT marker connector are mated, the CT marker is maintainable in the fixed CT marker spatial relationship. The tag engaging surfaces can also include a first tag connector having a tag connector geometry configured to detachably mate with a second tag connector geometry of a second tag connector provided by the corresponding surfaces of the tag such that, when the first tag connector and the second tag connector are mated, the tag is maintainable in the fixed tag spatial relationship.

In some embodiments, the first CT marker connector and the first tag connector may be the same.

In some embodiments, the apparatus may further include the CT marker and the tag. The CT marker can be detachably attachable to the arm and include a fiducial housing that houses the fiducial, where the fiducial can be shaped to allow the pose of the CT marker to be uniquely determinable in the volumetric CT image. The tag can be detachably attachable to the arm and measurable by the pose measurement system to determine the pose of the tag in the reference coordinate space. The pose of the fiducial if the CT marker were attached to the arm can be determinable from the measured pose of the tag when the tag is attached to the arm and the CT marker is detached from the arm.

In some embodiments, only one of the tag and the CT marker is attachable to the arm at any given time.

In some embodiments, the apparatus may also include a rigid detachable coupling for detachably attaching the fixation portion to at least one of the CT marker and the tag. The rigid detachable coupling may only be usable to attach the arm to the CT marker when the CT marker engaging surfaces are aligned with and in contact with the corresponding surfaces of the CT marker at the CT marker connection region and may be otherwise inoperable to attach the arm to the CT marker, and the rigid detachable coupling may only be usable to attach the arm to the tag when the tag engaging surfaces are aligned with and in contact with the corresponding surfaces of the tag at the tag connection region and may be otherwise inoperable to attach the arm to the tag.

In some embodiments, the CT marker may have a central portion and at least one CT marker arm extending from the central portion, the corresponding surfaces of the CT marker can be located within the central portion and, when the arm is detachably attached to the CT marker with the CT marker engaging surfaces in contact with the corresponding surfaces of the CT marker at the CT marker connection region, the at least one CT marker arm may extend towards the link portion.

In some embodiments, each CT marker arm may include a link engaging member, and when the link portion is softened for molding and the arm is detachably attached to the CT marker with the CT marker engaging surfaces in contact with the corresponding surfaces of the CT marker at the fiducial connection region, the link engaging member can be engageable with a surface of the link portion to deform the surface and provide a corresponding indentation in the surface such that when the link portion is hardened and the arm is detachably attached to the CT marker with the CT marker engaging surfaces in contact with the corresponding surfaces of the CT marker at the CT marker connection region, the link engaging member is receivable in the corresponding indentation to restrain movement of the CT marker arm relative to the link portion.

In accordance with another embodiment, there is provided a method for mapping a selected position on or within a human jaw to a corresponding position in a volumetric CT (computerized X-ray tomography) image of that jaw. The method can include providing a moldable retainer appliance and molding the retainer appliance to have an appliance geometry that mates with a surface geometry of at least a portion of the human jaw, such that when mated to the human jaw, the retainer appliance resists displacement relative to the human jaw. The method can further include hardening the appliance to retain the appliance geometry and resist deformation. The method may also include providing an arm that has a moldable link portion and a rigid fixation portion and rigidly attaching the link portion to the retainer appliance to maintain a fixed spatial mapping between the fixation portion and the retainer appliance to provide a fabricated appliance. The method may include detachably and rigidly attaching a CT marker including a fiducial detectable in the volumetric CT image to the fixation portion at a CT marker connection region to provide an imaging appliance including the fabricated appliance and the CT marker, attaching the imaging appliance to the human jaw, scanning the human jaw with the imaging appliance attached thereto to obtain the volumetric CT image of at least a portion of the fiducial and a portion of the human jaw in the volumetric CT image, detecting the pose of the fiducial in the volumetric CT image to derive a fiducial-to-image coordinate mapping, and detaching the CT marker from the fixation portion to provide the fabricated appliance. The method may further include detachably and rigidly attaching a pose-trackable tag to the fixation portion at a tag connection region to provide a tracking appliance including the fabricated appliance and the tag, wherein a configuration of the tag connection region relative to the CT marker connection region ensures a fixed tag-to-fiducial coordinate mapping prior to attaching any one of the tag and the CT marker, determining a tag-to-image coordinate mapping using the tag-to-fiducial coordinate mapping and the fiducial-to-image coordinate mapping, attaching the tracking appliance to the human jaw, determining a pose of the tracking appliance using a pose measurement system, determining tag coordinates of the selected position in a coordinate system of the tag using the pose of the tracking appliance, and mapping the tag coordinates of the selected position to a corresponding position in the volumetric CT image using the tag-to-image coordinate mapping.

In some embodiments, the link portion can be rigidly attached to the appliance by heating the link portion to a link transition temperature such that the link portion becomes soft and malleable, placing the link portion into contact with the retainer appliance, securing the link portion to the retainer appliance, and hardening the link portion to remain rigid and resist deformation such that the link portion is rigidly attached to the appliance and maintains the fixed spatial mapping between the fixation portion and the retainer appliance.

In some embodiments, the method may further include detachably and rigidly attaching the CT marker to the fixation portion at the CT marker connection region prior to attaching the link portion to the retainer appliance and placing the link portion into contact with the retainer appliance and securing the link portion to the retainer appliance by rigidly fixing an end of the softened link portion to the retainer appliance, pushing the arm, with the CT marker attached thereto, in a direction towards the appliance such that the softened link portion is molded to allow the fixation portion to be fixed in a support position relative to the retainer appliance such that at least a portion of the fiducial will appear in the volumetric CT image of the human jaw when the imaging appliance is attached to that jaw, and hardening the link portion such that the link portion is rigidly attached to the appliance with the fixation portion in the support position.

In some embodiments, securing the link portion to the retainer appliance comprises gluing the link portion to the retainer appliance.

In some embodiments, molding the retainer appliance to have the appliance geometry can include heating the retainer appliance to a retainer transition temperature such that the retainer appliance becomes soft and malleable, and pushing the softened retainer appliance into contact with the at least a portion of the human jaw having the surface geometry.

In some embodiments, the method may further include heating the link portion to a link transition temperature such that the link portion becomes soft and malleable, detachably and rigidly attaching the CT marker to the fixation portion at the CT marker connection region, the CT marker having at least one link engaging member, molding the link portion by pushing the at least one link engaging member into a surface of the link portion so that the at least one link engaging member deforms the surface of the link portion to provide at least one indentation corresponding to the at least one link engaging member, and hardening the link portion such that, when the CT marker is detachably attached to the fixation portion at the CT marker connection region, each link engaging member is receivable within the corresponding indentation and the CT marker is thereby restrained from moving relative to the link portion.

In accordance with another embodiment, there is provided a kit for mapping a selected position on or within a human jaw to a volumetric CT (computerized X-ray tomography) image of that human jaw. The kit may include a retainer appliance configured to be moldable to an appliance geometry that mates with a surface geometry of at least a portion of the human jaw, such that when mated with the human jaw, the retainer appliance resists displacement relative to the human jaw, the retainer appliance being further configured to be hardenable to remain rigid and resist deformation once molded to the appliance geometry. The kit may also include an arm having a moldable link portion and a rigid fixation portion, the link portion being rigidly attachable to the retainer appliance and hardenable to remain rigid and resist deformation once hardened to maintain a fixed spatial mapping between the fixation portion and the retainer appliance when the link portion is rigidly attached to the retainer appliance, the rigid fixation portion including a CT marker connection region and a tag connection region. The kit may further include a CT marker that is detachably attachable to the arm at the CT marker connection region and includes a fiducial detectable in the volumetric CT image, the fiducial shaped to allow a pose of the fiducial to be uniquely determinable in the volumetric CT image. The kit may also include a tag that is detachably attachable to the arm at the tag connection region, the tag being measureable by a pose measurement system to determine a pose of the tag in a reference coordinate space. The pose of the tag connection region relative to a pose of the CT marker connection region can have a substantially fixed tag-to-fiducial coordinate mapping that is determinable prior to attaching any one of the tag and the CT marker.

BRIEF DESCRIPTION OF THE DRAWINGS

Several embodiments will now be described in detail with reference to the drawings, in which.

Figure 1A:
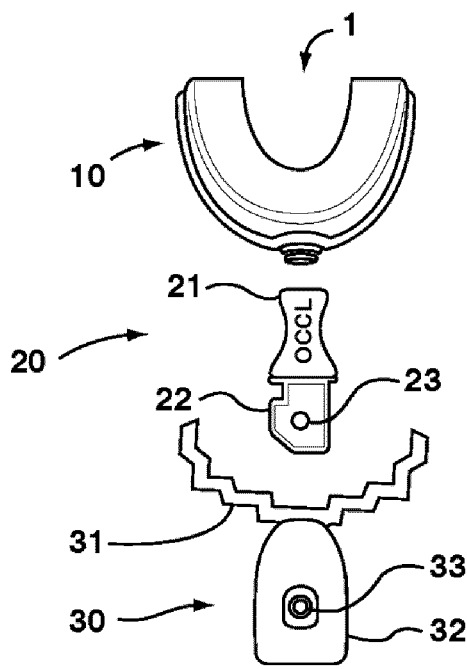
FIGS. 1A and 1B illustrate a top and bottom view of an example embodiment of a retainer appliance, an arm, and a CT marker.
Figure 1B:
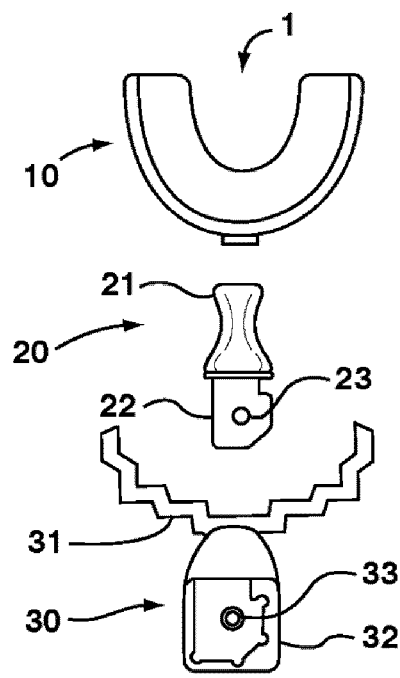

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DESCRIPTION OF EXAMPLE EMBODIMENTS

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that the term "coupled" used herein indicates that two elements can be directly coupled to one another or coupled to one another through one or more intermediate elements.

In embodiments, aspects of methods described herein, such as method 1200 described with reference to FIG. 12 below, may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example and without limitation, the programmable computer (referred to below as data processor) may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and combination thereof.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

The various embodiments described herein generally relate to an apparatus, kit and associated methods for registering a human jaw with a volumetric CT image of the human jaw and mapping a selected position on or within the human jaw to a corresponding position in the CT image. The embodiments described herein may include an apparatus configured for repeatedly and detachably attaching rigid structures (such as a CT marker and/or a trackable tag) in a fixed and stable geometrical relationship with a patient's jaw and registering and tracking the position of the human jaw. Embodiments of the apparatus, kit and methods described herein may provide various advantages as compared with previous approaches to registering a human jaw with a scanned image and guiding surgical navigation.

For example, embodiments of the apparatuses described herein may be fabricated more easily, rapidly, and reliably than prior known appliances. In some cases, fabrication of an appliance and verification of fit with the human jaw of the patient can be completed within a few minutes. The fabricated appliance may be able to securely mate with the surface geometry of the human jaw such that it resists displacement relative to the human jaw. The fabricated appliance may also provide surfaces for aligning and contacting rigid structures (i.e. CT markers and trackable tags) so that those rigid structures can be repeatably and detachably attached to the fabricated appliance with a pose (i.e. position and orientation) relative to the fabricated appliance that is known and fixed.

The secure mating between the appliance and the jaw may be obtained by initially providing a moldable retainer appliance. The retainer appliance can be configured for molding into an appliance geometry shaped to mate with a surface geometry of at least a portion of the human jaw. The retainer appliance may be manufactured of a moldable material that can be softened for molding. For instance, the moldable material may a transition temperature low enough to allow the retainer appliance to be molded directly in a patient's mouth without causing pain or damage to the patient's mouth. For instance, the transition temperature of the retainer appliance may be such that the retainer appliance can be softened in hot water, e.g. in the range of 40° C. to 80° C. When being molded, the retainer appliance can be pressed around and into contact with at least a portion of a surface of the human jaw or a facsimile thereof to mold the retainer appliance to the appliance geometry that mates with the jaw.

The moldable material may be hardenable to retain the molded shape and resisting deformation. After molding to the appliance geometry, the retainer appliance can be hardened to remain rigid and resist deformation. This may allow the retainer appliance to resist displacement relative to the human jaw when attached thereto. In some cases, when the retainer appliance is mated to the human jaw for use in registration or surgical navigation procedures, screws or dental adhesive may be used to secure the mating between the retainer appliance and the human jaw. This may be desirable, for instance, where the patient does not have enough teeth to provide a secure mating with the fabricated appliance based on the appliance geometry alone.

The apparatus also includes an arm having a moldable link portion and a rigid fixation portion. The moldable link portion can be rigidly attachable to the retainer appliance to provide a fabricated appliance that includes the retainer appliance and the arm. After rigidly attaching the link portion to the retainer appliance, the link portion can maintain a fixed spatial mapping between the fixation portion and the retainer appliance.

The rigid fixation portion can provide engaging surfaces for aligning, contacting and rigidly and detachably attaching a rigid structure. In some cases, only one rigid structure may be detachably attached to the rigid fixation portion at any given time. These surfaces may include guide and alignment portions to properly guide and align the rigid structures for detachable attachment. In some cases, the rigid fixation portion may include mating connectors or other securement mechanisms, such as bores for screws, to allow the rigid structures to be secured in place once properly aligned. The mating connectors may ensure that the rigid structures are properly aligned when detachably attached to the fixation portion.

The surfaces of the rigid fixation portion enable highly repeatable attachment of a rigid structure, such as a CT marker or a tag, to the fabricated appliance. The engaging surfaces can be configured to attach each rigid structure to the apparatus such that the rigid structure is maintained in a fixed spatial relationship with the apparatus. At the same time, the engaging surfaces allow rigid structures to be easily detached from the fabricated appliance and permit other rigid structures to be detachably attached.

The apparatus (or a kit including the apparatus) may also include a CT marker. The CT marker can be used to register the position of a human jaw with a scanned image of the human jaw, such as a volumetric CT (computerized X-ray tomography) image. The CT marker may include one or more fiducial markers that are detectable in the volumetric CT image. The fiducial markers can be shaped to allow a pose of the CT marker to be uniquely determined in the CT image. For instance, the fiducial may take the shape of the various fiducial bodies described in PCT Application No. PCT/CA2015/050025. In some cases, the fiducial markers may include a plurality of spheres that can be used to determine the pose of the CT marker.

The CT marker can be configured to be detachably attached to the fabricated appliance such that the fiducial body is positioned close to the human jaw when an image of the human jaw is taken. The pose of the fiducial body can be reliably determined from distinct features of the fiducial body detected in a scanned image of the human jaw, such as by the methods described in PCT Application No. PCT/CA2015/050025 and PCT Application No. PCT/CA2011/001294 mentioned above. As will be explained below, the moldable link portion may also allow a user to optimize the position of the CT marker (and in turn the fiducial body) relative to the jaw.

The CT marker may include a fiducial housing, within which the one or more fiducials can be contained. When the fiducial is contained within the fiducial housing, the fiducial can be secured in a fixed spatial relationship with the fiducial housing. When the CT marker is attached to the retainer appliance, exposed portions of a fiducial may include corners that could cause pain and discomfort to patients. A fiducial housing, within which the fiducial is contained, may provide a protective barrier between the fiducial and the patient to reduce pain or discomfort when the CT marker is in contact with the patient's lips or tissues.

The CT marker may also include a CT marker connector that can be used to detachably attach the CT marker to the fabricated appliance. The CT marker connector may be detachably attachable to the rigid fixation portion so that it can be attached and detached from the fabricated appliance as desired.

When the CT marker is attached to the fabricated appliance, a patient's lips and surrounding tissues may apply a substantial force against the CT marker. This force may make it difficult to mold the retainer appliance around the surface of the human jaw in order to obtain the desired appliance geometry. This can be particularly difficult for the lower jaw as the patient's lips and surrounding tissues can push the fabricated appliance upwards and off the jaw. In order to counteract the force while the retainer appliance hardens, a user may be required to apply pressure to the retainer appliance, in a direction towards the jaw. Detaching the CT marker from the retainer appliance may allow a patient to close their mouth during hardening, which can eliminate difficulties with proper seating of the retainer appliance on the jaw. Subsequently, the CT marker can be attached or re-attached to the fabricated appliance for registration of the jaw with an image of the jaw. The engaging surfaces of the rigid fixation portion may permit detachable attachment and re-attachment, with the CT marker in a consistent spatial relationship with the retainer appliance.

It may also be desirable to remove the CT marker from the fabricated appliance when performing a surgical navigation procedure. For example, the CT marker may obstruct the procedure or cause discomfort to the patient. If the CT marker is left connected to the fabricated appliance during surgery on a patient's jaw, the CT marker may press against the patient's lips or mouth and prevent the fabricated appliance from properly mating with or sitting against the human jaw and teeth. This could lead to inaccurate reading or tracking of the position of the jaw during surgery.

Furthermore, having a CT marker fixed on the fabricated appliance during surgery may impede the movement of surgical tools, such as a dental handpiece. The ability to remove the CT marker may reduce or eliminate interference with the movement of surgical tools and instruments. This can provide a surgeon with more freedom to move and operate. The CT marker engaging surfaces of the rigid fixation portion may allow the CT marker to be attached and detached from the retainer appliance as desired.

Furthermore, in embodiments described herein the apparatus may be fabricated using materials that can be easily cut using scissors. Accordingly, sections of the fabricated appliance may be quickly and precisely cut out using small scissors. This can allow unhindered access by surgical tools and instruments to target sites in the patient's jaw.

Embodiments described herein may also include a tag. In general, the tag can be configured to be measureable or trackable by a pose measurement system to determine a pose of the tag in a reference coordinate space. The tag may include a plurality of trackable portions disposed thereon, that can be tracked using various techniques such as optical or electromagnetic tracking techniques. The tag may also include a tag connector configured to be detachably attachable to the rigid fixation portion of the arm.

For a surgical procedure it may be desirable to attach a tag to the retainer appliance that is less obstructive than the CT marker, but nonetheless allows for tracking the position of the tag relative to the jaw. Tracking the position of the tag relative to the jaw may require a known relationship between the pose of the tag when it is attached to the fabricated appliance and the pose of the CT marker when it is attached to the fabricated appliance. That is, the pose of the tag connector relative to the pose of the CT marker connector may be known and fixed prior to attaching any one of the tag and the CT marker to the fabricated appliance. The engaging surfaces of the rigid fixation portion may ensure that this relationship is known and fixed prior to using either the CT marker or the tag.

Using the same rigid fixation portion to attach both the CT marker and a tag assembly to the apparatus allows a relative mapping between the CT marker and the tag assembly to be predefined. That is, the relative positions of the CT marker and the tag assembly when they are respectively connected to the apparatus can be known in advance for each apparatus. In some cases, the engaging surfaces of the rigid fixation portion may include separate engaging surfaces for the CT marker and the tag. In other cases, the same engaging surfaces may be used to attach and detach both the CT marker and the tag.

A relative mapping between the position of the tag and the position of the CT marker when each is detachably attached to the fabricated appliance can thus be stored as a tag-to-fiducial coordinate mapping. This stored tag-to-fiducial coordinate mapping may allow the tag to be used to determine a position of the interior of the human jaw based on the stored spatial relationship and the measured pose of the tag.

The stored coordinate mapping can be used to implement an automated registration method, such as the registration method described in PCT Application No. PCT/CA2011/001294 mentioned above. The predefined coordinate mapping (or fixed spatial relationship) provided by using the rigid fixation portion to detachably attach both the tag and the CT marker may enable the automated registration method to be carried out without requiring the tag assembly and the CT marker to be connected to each other, or simultaneously connected to the apparatus.

Furthermore, using a consistent structure for the rigid fixation portion as well as the connectors for the tag assembly and the CT marker may allow the tag and CT marker to be re-used with fabricated appliances molded to mate with jaws of different patients.

Reference is first made to FIG. 1, shown therein is an example embodiment of the various components of an apparatus 1 prior to fabrication for a specific patient. In the embodiment shown, the apparatus 1 includes a retainer appliance 10 and an arm 20. The apparatus 1 may also be provided in a kit along with a CT marker 30. FIGS. 1A and 1B show top and bottom views respectively of this example embodiment of apparatus 1.

The arm 20 may include a moldable link portion 21 and a rigid fixation portion 22. The moldable link portion 21 can be rigidly attached to the retainer appliance 10. The link portion 21 may be molded to provide a desired support position for the rigid fixation portion 22. The support position may be adjusted to ensure at least a portion of the fiducial of CT marker 30 will be visible in a scanned image of the patient's jaw. When the arm 20 is rigidly attached to the retainer appliance 10, the apparatus 1 may be referred to as a fabricated appliance.

The CT marker 30 may also be detachably attached to the arm 20. When the CT marker 30 is detachably attached to the arm 20 of the fabricated appliance, and the retainer appliance 10 (and link portion 21) is molded and hardened, the apparatus 1 may be referred to as an imaging appliance.

The rigid fixation portion 22 may include engaging surfaces to align and contact the CT marker 30 and/or a tag (not shown in FIG. 1) for attachment. The engaging surfaces may indicate a connection region, align the connection region with corresponding surfaces of the CT marker 30 (or a tag), and contact the corresponding surfaces of the CT marker 30 (or tag) to allow the CT marker 30 (or tag) to be detachable attached to the fabricated appliance.

When the arm 20 is detachably attached to the CT marker 30 with the engaging surfaces of the fixation portion 22 in contact with the corresponding surfaces of the CT marker at the connection region the CT marker 30 can be maintained in a fixed spatial relationship with the arm 20. A pose of the fixation portion 22 may then be determined from the pose of the CT marker 30. In some cases, the fixation portion 22 may include separate engaging surfaces for the CT marker 30 and a tag, while in other cases the same engaging surfaces may be used.

The engaging surfaces of the fixation portion 22 may include a connector having a connector geometry shaped to detachably mate with a corresponding connector provided by the corresponding surfaces of the CT marker 30. In the example shown in FIG. 1, the connector provided by the engaging surfaces is a male connector; however, in other embodiments, the rigid fixation portion 22 may include a female connector.

Figure 4A:
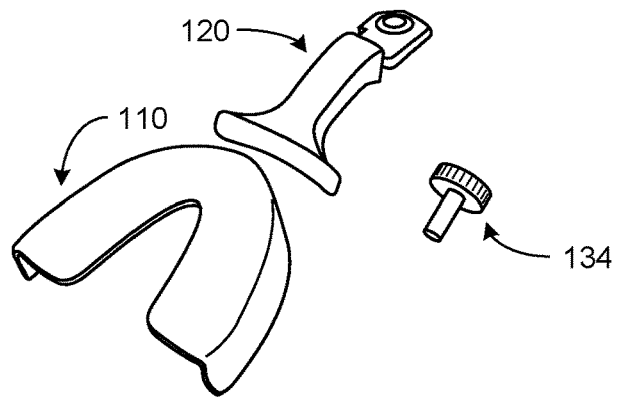
FIGS. 4A to 4B illustrate perspective views of a second example embodiment of a retainer appliance and arm.

In some cases, the rigid fixation portion 22 of the arm 20 may also provide a bore 23 for accepting a screw 34 (e.g. as shown in FIGS. 4A and 6D). The screw 34 may be used to secure the rigid fixation portion 22 to the CT marker 30 or a tag to further ensure that the CT marker 30 or the tag remains attached securely in place. In some cases, the screw 34 may be a thumb screw. In some cases, the screw 34 may be disposable.

The CT marker 30 may include a fiducial 31 and a connector 32. The connector 32 can be configured to releasably mate with the connector provided by the rigid fixation portion 22. In the embodiment shown, the connector 32 is a female connector. In other embodiments, the connector 32 may be a male connector. The connector 32 may also provide a bore 33 for accepting a screw 34 (shown in FIG. 4). The screw 34 may be used to further secure the CT marker 30 to the rigid fixation portion 22.

Figure 1C:
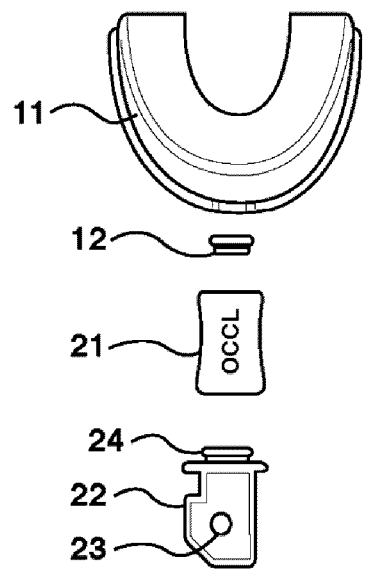
FIG. 1C illustrates a top exploded view of the retainer appliance and arm shown in FIG. 1A.

FIG. 1C shows an exploded top view of the retainer appliance 10 and arm 20. In some cases, the retainer appliance 10 may include a retainer sheet 11 and a rigid retainer connector 12. The rigid retainer connector 12 may be located in an easily accessible area. For example, where the retainer appliance 10 is shaped to conform to the surface geometry of a patient's jaw, the rigid retainer connector 12 may be provided at a position facing outward from the front of the patient's mouth.

The rigid retainer connector 12 can be configured to attach the arm 20 and the retainer appliance 10 when the arm 20 is positioned in contact with the retainer appliance 10. In order to retain the arm 20 in place, the rigid retainer connector 12 of the retainer appliance 10 may have two segments of different sizes. For example, as shown in FIG. 1C, the segment of the rigid retainer connector 12 disposed along the retainer sheet 11 may be larger than the segment abutting the moldable link portion 21.

The moldable link portion 21 can be positioned to contact the retainer appliance 10 at the rigid retainer connector 12. The arm 20 can then be secured to the retainer appliance 10, e.g. using an adhesive.

In some cases, the moldable link portion 21 may be manufactured of a moldable material, such as a thermoplastic material. In such cases, the moldable link portion 21 may be softened and rendered malleable by heating the link portion 21 to the transition temperature of the moldable material. As with the retainer appliance 10, the moldable link portion 21 may have a transition temperature sufficiently low (e.g. 40° C. to 80° C.) to allow the link portion 21 to be molded while in close proximity to the patient's mouth.

A variety of thermoplastic materials can be used for the retainer sheet 11 and/or the moldable link portion 21, such as those available for orthopedic splinting from companies such as Algeos and Patterson Medical®. In some embodiments, the moldable material can have low or no "shape memory". Shape memory generally refers to the tendency that a material returns to its original shape when being molded. Accordingly, an appliance fabricated using such a moldable material may resist deformation after being molded to its desired shape and being hardened.

The material used for the retainer appliance (i.e. retainer sheet 11) and/or link portion 21 may also have low thermal conductivity. This can allow retainer sheet 11 to retain heat in order to be remain soft and malleable when being shaped. This can also avoid burning tissues of a human jaw when pressing the retainer appliance around the human jaw for shaping. In such cases, a higher transition temperature may be used while still allowing the retainer appliance 10 and/or link portion 21 to be molded in close proximity to or in contact with the patient's mouth.

When the arm 20 is being mounted to the retainer appliance 10, the end of the softened link portion 21 may be secured to the retainer appliance and then the arm 20 can be pushed towards the retainer appliance 10 to mold the moldable link portion 21 to allow the rigid fixation portion 22 to be mounted in a support position. The moldable link portion 21 can then be hardened to retain its mounted position and provide a fabricated appliance.

In some cases, the CT marker 30 can be detachably attached to the rigid fixation portion 22 prior to mounting and securing the arm 20 on the retainer appliance 10. In such cases, the CT marker 30 and the arm 20 can be pushed towards the retainer appliance 10 so that the support position of the rigid fixation portion 22 ensures that at least a portion of the fiducial 31 will appear in a volumetric image of the human jaw when the imaging appliance is mounted on the jaw. The moldable link portion 21 may then be hardened to remain rigid and resist deformation. In various embodiments, the moldable link portion 21 can be mounted to the retainer appliance 10 before or after the retainer appliance 10 has been hardened.

In some embodiments, the moldable link portion 21 may also be marked with an orientation indicator. In the example shown in FIG. 10, the orientation is indicated by the letters "OCCL" (e.g. occlusion) because the apparatus 1 is directed to an appliance for a human jaw. In some cases, the orientation marker can be used to determine whether the fabricated appliance is being used with the upper jaw or the lower jaw. The moldable link portion 21 may also include an arm connector segment 24 to retain the moldable link portion 21 in connection with the rigid fixation portion 22. The moldable link portion 21 may be mounted on the rigid fixation portion 22 at the arm connector segment 24 to form the arm 20. Typically, the link portion 21 and the fixation portion 22 will be fixed to one another prior to attaching the arm 20 to the retainer appliance 10.

Figure 1D:
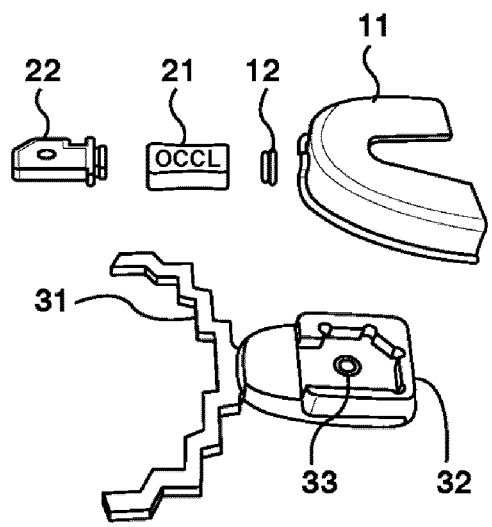
FIG. 1D illustrates a perspective view of the retainer appliance, arm, and CT marker shown in FIG. 1A.

FIG. 1D shows a perspective view of the retainer appliance 10, the arm 20 and CT marker 30. As can be seen in FIG. 1D, the connector 32 can be configured to mate with a connector of the rigid fixation portion 22 to secure the CT marker 30, and thus the fiducial 31 in a fixed spatial relationship with the arm 20.

Figure 2A:
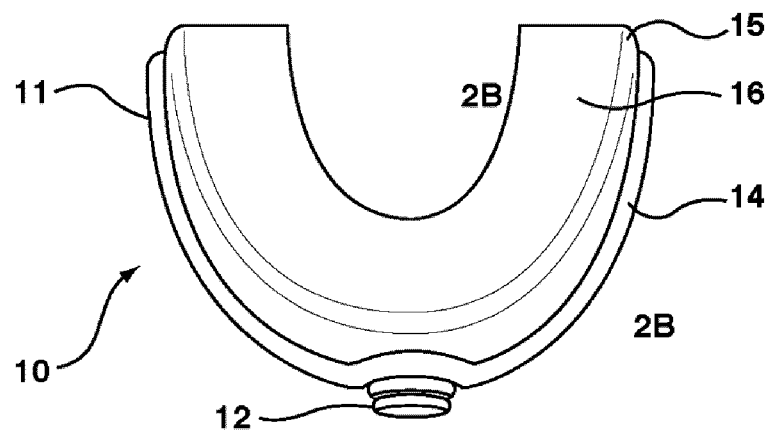
FIG. 2A illustrates a perspective view of an example embodiment of a retainer appliance.
Figure 2B:
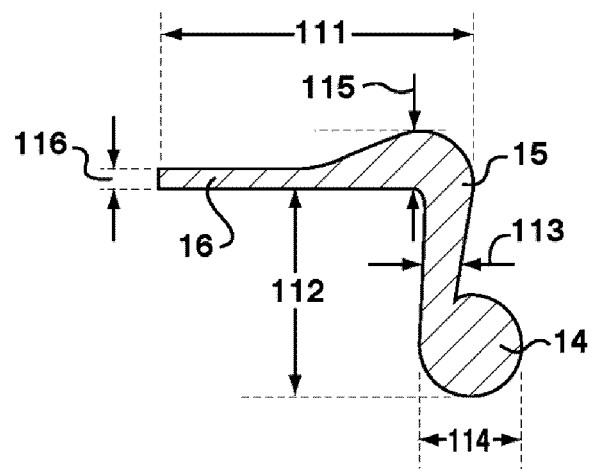
FIG. 2B illustrates a cross-sectional view of an example embodiment of a retainer appliance along the section 2B shown in FIG. 2A.

FIGS. 2A and 2B show another example embodiment of a retainer appliance 10. The perspective view shown in FIG. 2A illustrates a retainer appliance 10 including the retainer sheet 11 and the rigid retainer connector 12. The retainer sheet 11 may include a number of regions having varying thickness. In regions of greater thickness, the retainer sheet 11 may be stronger and more rigid while in regions of lesser thickness, the retainer sheet 11 may be more flexible. In the example shown in FIG. 2A, the retainer sheet 11 includes a spine 14, a vertical wall region 15, and a top surface region 16.

FIG. 2B shows a cross-section of the example retainer sheet 11 of FIG. 2A along cross-section 2B. The spine 14 is shown as a tubular region disposed along the base of the retainer sheet 11. In some embodiments, the spine 14 may have a maximum width 114 that can be about 4 millimeters.

In some embodiments, the rigid retainer connector 12 may be connected directly to the spine 14. The thickness of the spine 14 may provide stability for the rigid retainer connector 12 when the moldable link portion 21 is mounted to the retainer appliance 10. Furthermore, the thickness of the spine 14 may also ensure that the retainer appliance 10 maintains its overall shape.

The top surface region 16 may comprise a thin region disposed along the top of the retainer sheet 11. In this example embodiment, the top surface region 16 may have a minimum thickness 116 of about 1 millimeter and a maximum thickness 115 of about 2-3 millimeters. The top surface region 16 can be designed to easily conform to the surface of the human jaw during molding. As shown in FIG. 2A, the retainer appliance 10 has been configured to conform to the surface of a human jaw. Accordingly, the top surface region 16 can be configured to conform to the lingual surface of the teeth.

The thinness of the top surface region 16 may provide flexibility to facilitate removal of the retainer appliance 10 from the surface of the human jaw during or after molding. In some cases, if the retainer appliance 10 has a much thicker and more rigid top surface region 16, the retainer appliance 10 may lock onto the surface of the human jaw.

The thinness of the top surface region 16 may also enable it to be cut more easily and precisely. For instance, the example retainer sheet 11 in FIGS. 2A and 2B may be cut using scissors having short blades of approximately 10 millimeters or less. This may facilitate surgery on a patient wearing the fabricated appliance as access is provided to regions that would otherwise be blocked or obscured by the fabricated appliance.

The vertical wall region 15 may have a slightly thicker region connecting the spine 14 and the top surface region 16. The vertical wall region 15 can be configured to enable the top surface region 16 to conform to the surface of the human jaw while the spine 14 provides stability by resting on the human jaw. In this example embodiment, the vertical wall region 15 may have a height 112 of about 9 millimeters and a thickness 113 of about 3 millimeters.

The thickness of the vertical wall region 15 may increase the overall stability of the retainer appliance 10 by preventing the vertical wall region 15 and the top surface region 16 from spreading apart too easily. The thickness of the vertical wall region 15 may also prevent tears if the human jaw is sharp. For instance, the vertical wall region 15 may conform to the buccal cusps (i.e. ridges) of the teeth, and the thickness of the vertical wall region 15 may prevent tears that could be caused by teeth of the human jaw.

Figure 3:
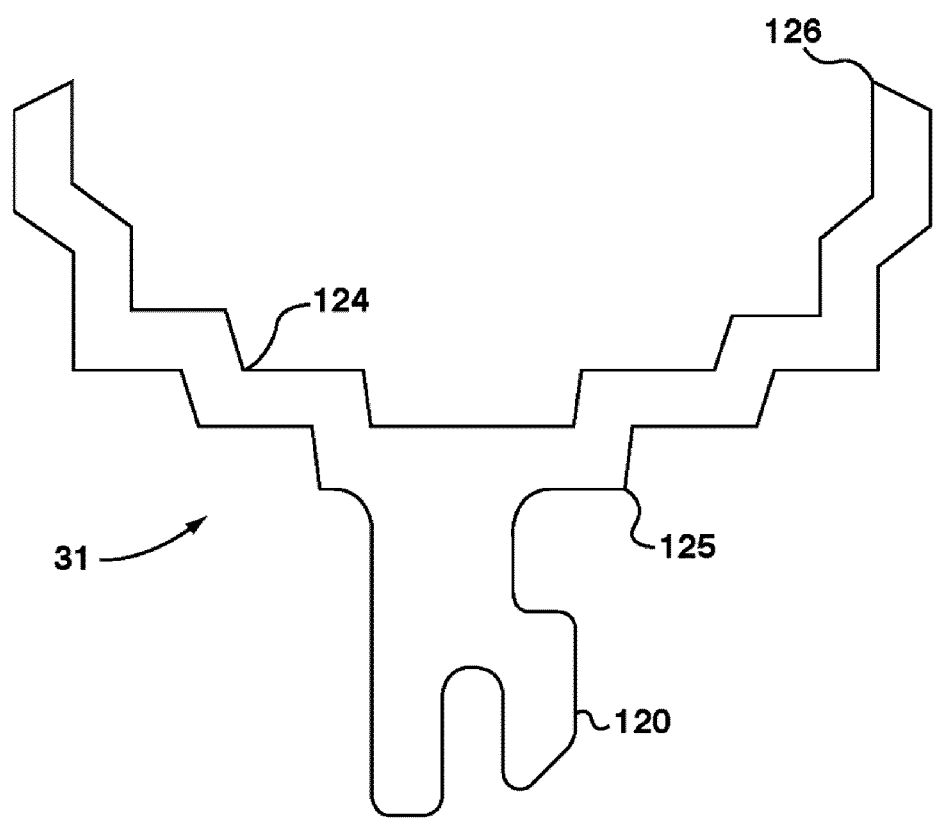
FIG. 3 illustrates a top view of an example embodiment of a fiducial body.

FIG. 3 shows an example embodiment of a fiducial 31. The fiducial 31 may be manufactured from a scan detectable material that provides contrast in scanned images, such as volumetric CT images, to the retainer appliance 11, moldable link portion 20, the human jaw, and air, but does not create image artifacts. In at least one embodiment, the fiducial 31 can be made of aluminum, titanium, aluminum alloy, or a low-density metal. This can allow the fiducial 31 to be identified when scanning the human jaw with a scanner such as a CT scanner.

The fiducial 31 may comprise a head 120 and an imaging portion that may be positioned proximal to the retainer appliance 10 during scanning. The head 120 can be configured to be rigidly attached to the connector 32 of the CT marker 30. In some embodiments, the connector 32 may be formed of plastic molded over the head 120 of the fiducial 31. In some embodiments, the CT marker 30 including the fiducial 31 and the connector 32 may be formed of a single material, such as aluminum. In some embodiments, the CT marker 30 may include a fiducial housing 139 (shown in FIG. 5), within which the fiducial 31 is contained. In embodiments where the CT marker 30 is formed of a single material or includes a fiducial housing, the fiducial 31 may not require a head 120 for attachment to the connector 32.

The imaging portion of the fiducial 31 may include a plurality of distinct features (e.g. 124, 125 and 126) so that the fiducial body 31 may be registered in a scanned image. The plurality of distinct features 124, 125 and 126 may enable a pose of the fiducial 31 to be uniquely determined by identifying at least some of the distinct features. The pose of the fiducial 31 can be reliably determined from the distinct features of the fiducial 31 detected in a scanned image of the human jaw, such as by using the methods described PCT Application No. PCT/CA2015/050025 mentioned above.

Figure 4B:
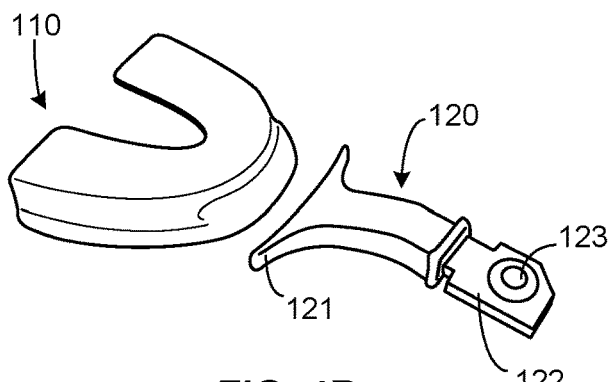

FIGS. 4A to 4B show another example embodiment of a retainer appliance 110, arm 120, and screw 134. Generally, retainer appliance 110 can be similar to retainer appliance 10 described above with the exception that retainer appliance 110 does not have an equivalent rigid retainer connector 12.

Figure 4C:
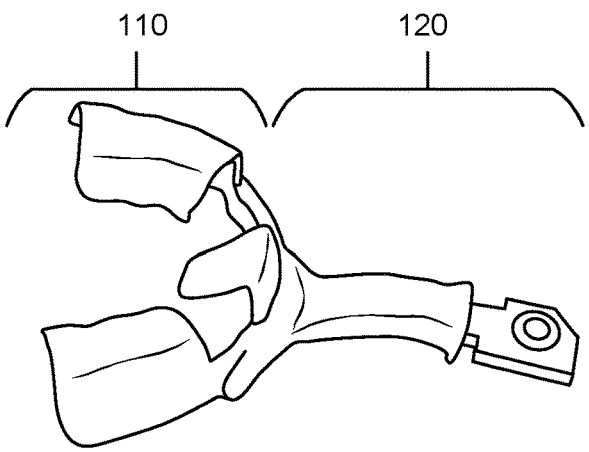
FIG. 4C illustrates a perspective view of a fabricated appliance in accordance with the example embodiment shown in FIG. 4A.

Arm 120 may include a moldable link portion 121 and a rigid fixation portion 122. Similar to rigid fixation portion 22 of arm 20, rigid fixation portion 122 can provide a fixed spatial relationship between the retainer appliance 110 and a rigid structure, such as a CT marker 30 or a tag 80, when the rigid structure is attached thereto. The rigid fixation portion 122 can also include a bore 123. As shown in FIGS. 4B and 4C, bore 123 may be surrounded by a ring-shaped protrusion. The ring-shaped protrusion may serve as an orientation marker, similar to the letters "OCCL" of FIG. 1, to identify whether the fabricated appliance is being used for the upper jaw or the lower jaw.

Link portion 121 can include a wing-shaped base. The base may be shaped to conform to the contour of the front of the retainer appliance 110 to provide greater surface area for securing the link portion 121 to the retainer appliance 110. The link portion 121 may be secured to the retainer appliance 110 using an adhesive, preferably a strong, fast curing adhesive, such as a cyanoacrylate-based glue. The link portion 121 can also be molded to the retainer appliance 110 by pressing the wing-shaped base towards the vertical wall region 15 of the retainer appliance 110. The link portion 121 may be molded in the same manner as with link portion 21.

FIG. 4C shows another example embodiment of a fabricated appliance. The fabricated appliance is provided by rigidly attaching the link portion 121 of the arm 120 to the retainer appliance 110. As shown in FIG. 4C, regions of the retainer appliance 110 may be removed prior to use of the fabricated appliance to allow a surgeon to access regions of interest in the patient's mouth.

Figure 5A:
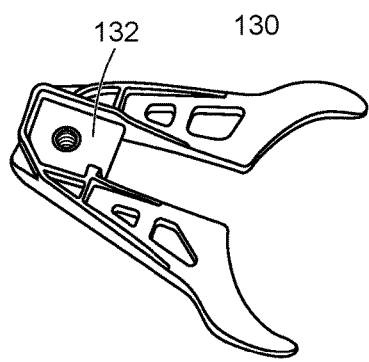
FIGS. 5A and 5B illustrate a top view and a top cut away view of an example embodiment of a CT marker.
Figure 5B:
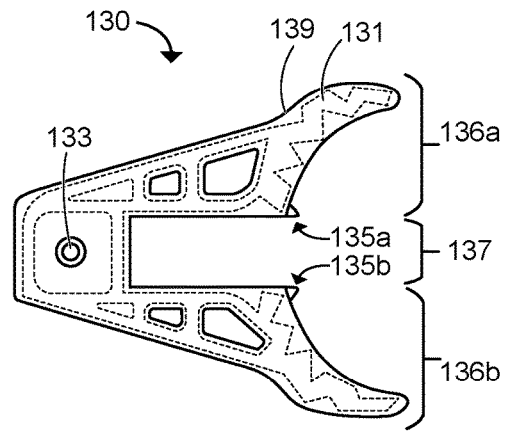

FIGS. 5A and 5B show another example embodiment of a CT marker 130. The CT marker 130 includes a fiducial 131 contained within a fiducial housing 139. The fiducial housing may include inner surfaces that correspond to the surfaces of the fiducial 130 so that the fiducial 130 remains in a fixed spatial relationship with the fiducial housing 139. The fiducial housing 139 may include outer surfaces that are round so if the outer surfaces come in contact with the patient's lips or tissues, pain and discomfort may be reduced. The fiducial housing 139 may be plastic.

The CT marker 130 may also include a mating connector 132. The connector 132 may be rigid. The connector 132 may also be formed of a plastic material. Similar to connector 32, the connector 132 can be configured to mate with the rigid fixation portion 122. The connector 132 may also provide a bore 133 for accepting a screw 134 (shown in FIG. 8A). The screw 134 may be used to further secure the connection between the connector 132 and the rigid fixation portion 122.

In some embodiments, the CT marker 130 may also provide link engaging members 135a and 135b. Link engaging members 135a and 135b may be protrusions, or spikes to engage with the base of the link portion 121 or with the retainer appliance 110. While the link portion 121 is soft and malleable (e.g. during molding of the link portion 121), the CT marker 130 may be connected to the rigid fixation portion 122 as well. The link engaging members 135a and 135b may engage with a surface of the wing-shaped base of the link portion 121 to deform the surface of the wing-shaped base of the link portion 121 and create indentations in the wing-shaped base of the link portion 121. When the link portion 121 hardens, these indentations may receive the link engaging members 135a and 135b to further secure the connection of the CT marker 130 to the arm 120 by restraining movement of the CT marker 130 with respect to the link portion 121 of the arm 120. Analogously, the link engaging members 135a and 135b could create indentations in the retainer appliance 110 that operate in a similar manner.

Figure 5C:
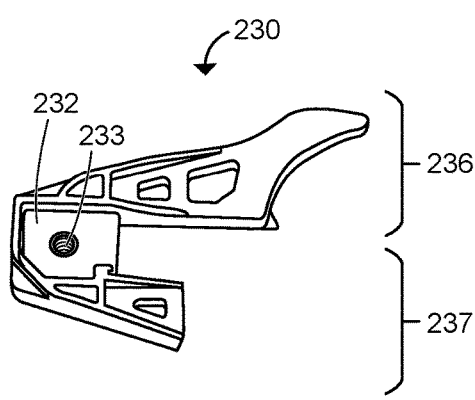
FIG. 5C illustrates a top view of another example embodiment of a CT marker.
Figure 5D:
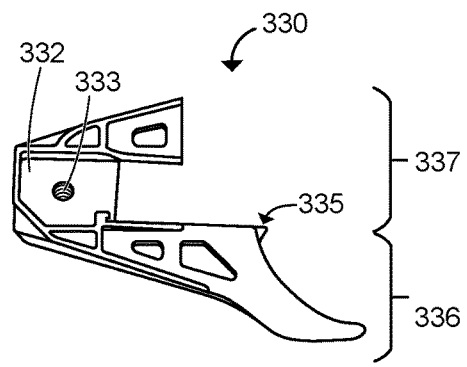
FIG. 5D illustrates a top view of a further example embodiment of a CT marker.

The CT marker 130, as shown in FIGS. 5A and 5B, include a central portion 137 and arms 136a and 136b each extending from the central portion. Each of the link engaging members 135a and 135b can be located on one of the CT marker arms 136a and 136b. In some embodiments, single-arm CT markers 230 and 330 may be used as shown in FIGS. 5C and 5D. The CT marker 230 in FIG. 5C has a central portion 237 and a single arm 236 extending from the central portion 237. Similarly, the CT marker 330 in FIG. 5D has a central portion 337 and a single arm 337 extending from the central portion 337. Single-arm CT markers 230 and 330 may be used to reduce discomfort for patients with smaller mouth openings. Single-arm CT markers 230 and 330 may also be used when only one side of the jaw is being treated.

Figure 6A:
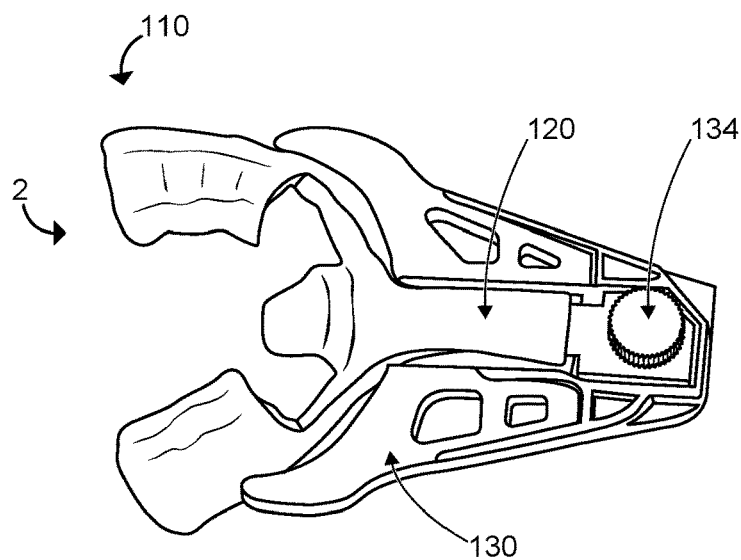
FIGS. 6A and 6B illustrate a top view and a perspective view of an example imaging appliance including the fabricated appliance of FIG. 4C and the CT marker shown in FIG. 5A.
Figure 6B:
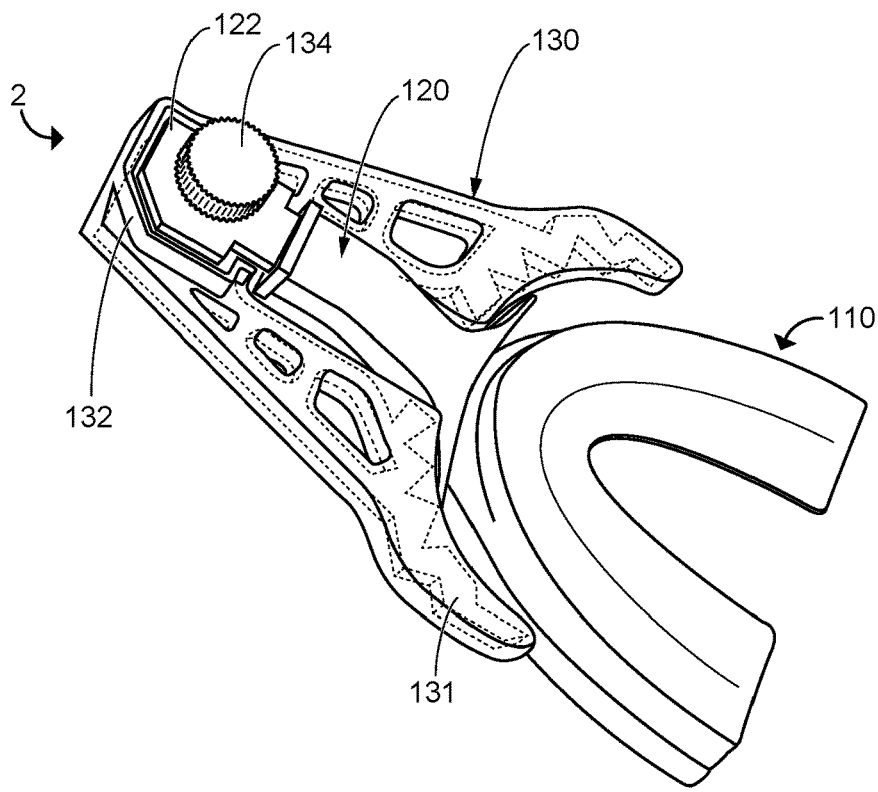

FIGS. 6A and 6B show an example embodiment of an imaging appliance 2 including a CT marker 130 with two arms detachably attached to a fabricated appliance (that includes an arm 120 and a retainer appliance 110). The rigid fixation portion 122 of the arm 120 can be mated with the connector 132 of the CT marker 130. A screw 134 may secure the rigid fixation portion 122 to the connector 132. The CT marker 130 may have a fiducial housing that extends along both CT marker arms and houses a fiducial 131.

Figure 7:
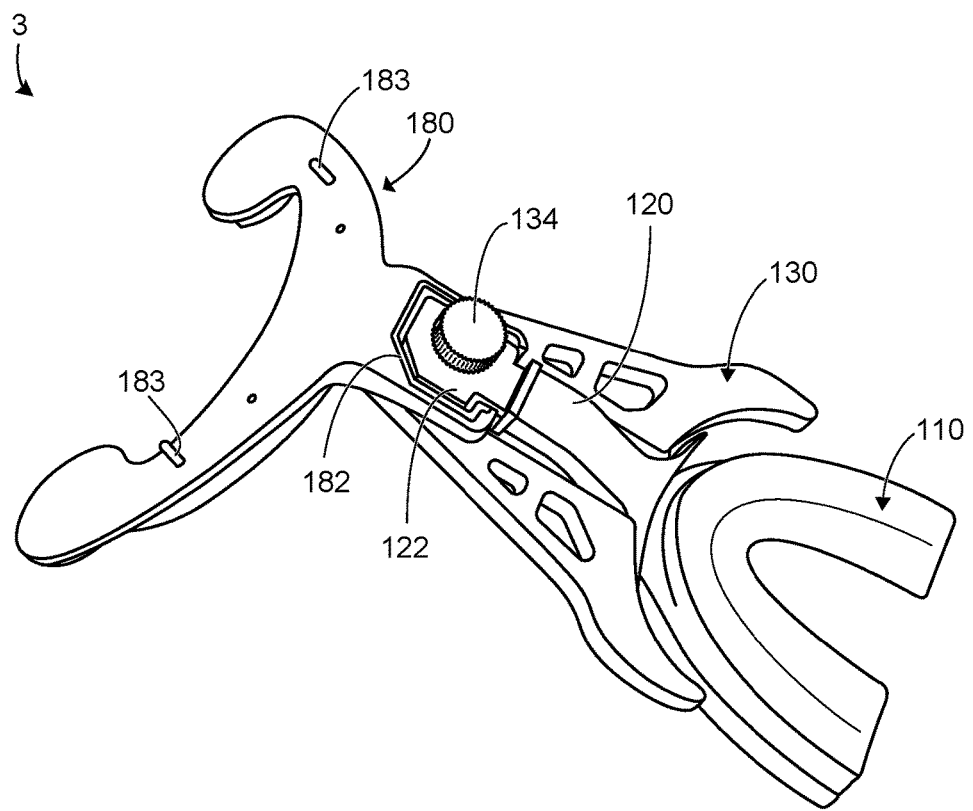
FIG. 7 illustrates a perspective view of an example tracking appliance including the fabricated appliance of FIG. 4C and a tag with an example CT marker shown to illustrate the relationship between the tag and the CT marker.

Referring now to FIG. 7, shown therein is an example embodiment of the fabricated appliance with a tag 180 attached thereto to provide a tracking appliance 3. The tag 180 may also be connected to the fabricated appliance using the rigid fixation portion 122. Although the tracking appliance 3 does not include a CT marker, the CT marker 130 is shown in FIG. 7 to illustrate the relationship between the pose of the CT marker 130 and the tag 180 when they are respectively attached to the arm 120.

The tag 180 can include a tag body 181 and a tag connector 182. The tag body 181 may include a plurality of trackable portions 183. In some cases, the trackable portions may include markings 84 and 85 (shown in FIG. 9D) that can be read by a various types of optical tracking devices such as the MicronTracker by ClaroNav Inc. In other cases, the trackable portions may be trackable electromagnetically or using other tracking techniques.

The tag connector 182 can be configured to mate with the rigid fixation portion 122. The tag assembly 180 can then be detachably attached to the fabricated appliance by releasably mating the tag connector 182 with the rigid fixation portion 122 such that the tag assembly 180 is maintained in a fixed spatial relationship with the fabricated appliance while connected thereto.

Similar to the connector 132, the tag connector 182 may also provide a bore 133 for accepting the screw 134. The screw 134 can be used to secure the tag 180 in place when detachably attached to the fabricated appliance to ensure that the tag 180 is held in its fixed and stable position.

In some cases, the tag 180 may be connected to the fabricated appliance by first detaching the CT marker 130. The tag assembly 180 can then be detachably attached to the fabricated appliance to provide a tracking appliance (see e.g.

Figure 10A:
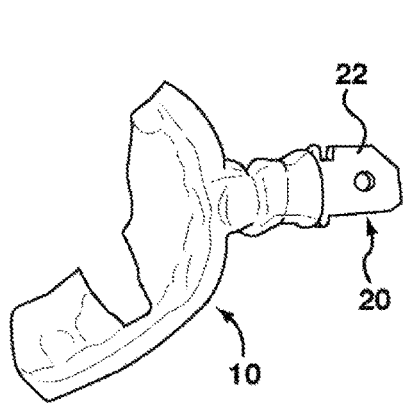
FIGS. 10A to 10D illustrate examples of steps of using a fabricated appliance with a CT marker and a tag assembly.
Figure 10B:
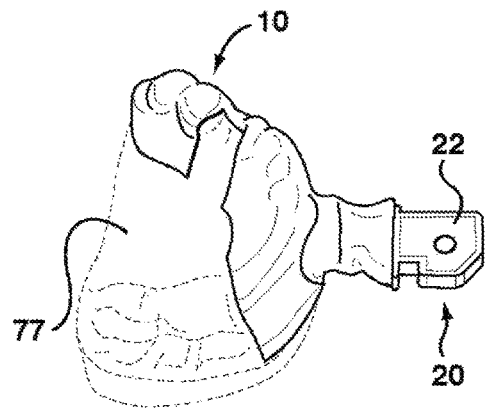
Figure 10C:
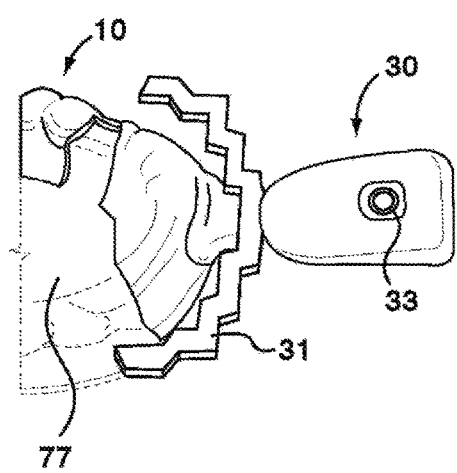
Figure 10D:
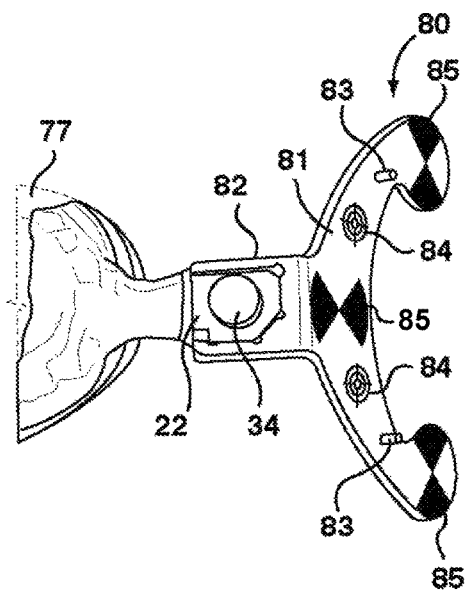

FIG. 10D). The orientation of the tag body 181 may then be uniquely determined based at least in part on the trackable portions 183.

FIG. 7 also shows a representation of CT marker 130, which is not attached to the tracking appliance 3. CT marker 130 is shown in FIG. 7 to illustrate the known and fixed spatial relationship between the CT marker 130 and the tag 180 that is provided by the engaging surfaces of the rigid fixation portion 122. The rigid fixation portion 122 can be used to detachably attach to both the connector 32 and the tag connector 182. The detachable connection provided by the rigid fixation portion 122 allows the spatial relationship between the position of the CT marker 130 on the fabricated appliance and the position of the tag assembly 180 on the fabricated appliance to be known and fixed in advance, and stored.

Figure 8:
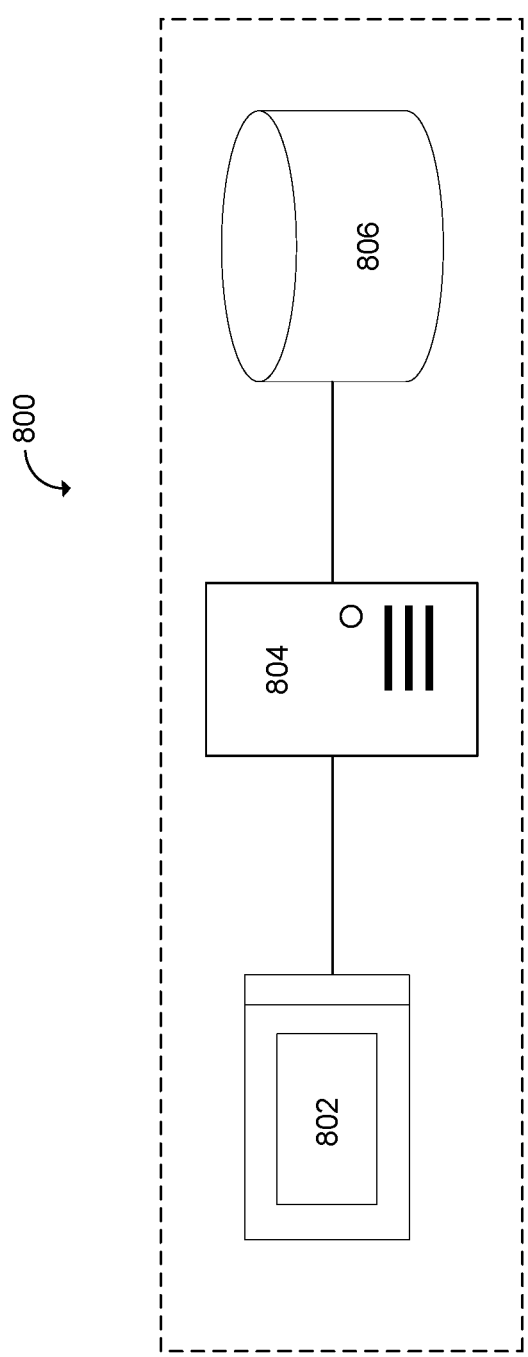
FIG. 8 illustrates an example embodiment of a system for registering a human jaw with a CT image of the human jaw.

Referring now to FIG. 8, shown therein is an example embodiment of a system 800 for registering a human jaw with a volumetric CT image of the human jaw. The system 800 may include a scanner 802, a data processor 804, and a database memory 806.

The scanner 802 can be configured for conducting a scan of the human jaw with an imaging appliance attached thereto, such as the various imaging appliances described herein. The scanner 802 can further be configured to generate a volumetric CT image that includes at least a portion of the human jaw and at least a portion of a fiducial of the imaging appliance in the volumetric image.

In some embodiments, the scanner 802 can be any suitable scanner for acquiring a volumetric tomography image of a human jaw and a fiducial proximate the human jaw. For example, the scanner 802 can be a tomographical scanner such as a CT (X-ray computed tomography) scanner.

The data processor 804 can be coupled to the scanner 802 and the database memory 806. In some cases, the data processor 804 may be located remotely from the scanner 802 and/or the database memory 806, while in other cases the components of the system 800 may be coupled locally. The data processor 804 can be configured to receive a scanned volumetric image from the scanner 802.

In some cases, the system 800 also includes a database memory 806. The database memory 806 can be configured to store a reference model of the fiducial 31, comprising the plurality of distinct features 124 to 126 in the reference fiducial coordinate system. Similarly, the database memory 806 may store a reference model of the tag.

Generally, the data processor 804 can be configured to detect the pose of the fiducial 31 in the volumetric image to derive a fiducial-to-image coordinate mapping. The fiducial-to-image coordinate mapping may indicate a mapping between the fiducial and the portion of the jaw in the volumetric CT image. The fiducial-to-image coordinate mapping may then be stored in the database memory 806. That is, the data processor 804 may determine a relative mapping between the pose of the fiducial 31 and the pose of the human jaw. The pose of the fiducial 31 may be determined based on the plurality of distinct features 124 to 126, or using various methods as described in PCT/CA2015/050025.

The database memory 806 may also store a tag-to-fiducial coordinate mapping for the arm that is used with the imaging or tracking appliance. The tag-to-fiducial coordinate mapping may correspond to a mapping between the pose of the tag connection region relative to the pose of the CT marker connection region. This may allow the pose of the fiducial to be determined from the pose of the tag, and then using the fiducial-to-image coordinate mapping, the relative positioning of the tag and the jaw can be determined.

The system 800 may also include a display to display to a user the scanned image of the human jaw and the fiducial, as well as to display the tracking of the human jaw during surgical navigation procedures.

Figure 11A:
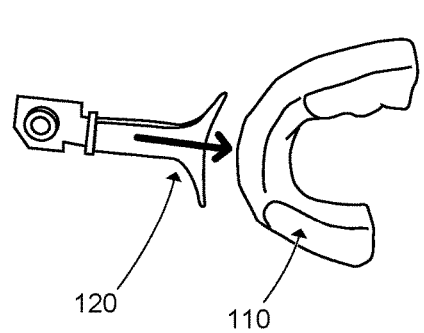
FIGS. 11A to 11H illustrate an example embodiment of a process for preparing an imaging appliance for use in registering a human jaw with a volumetric CT image of the human jaw.
Figure 11B:
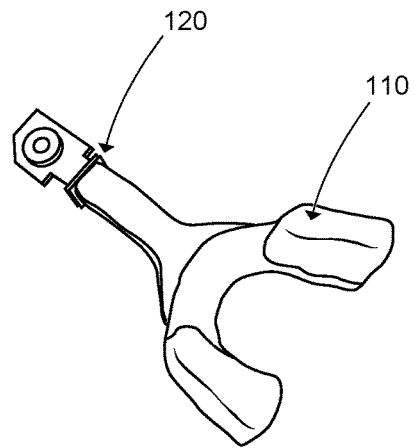
Figure 11C:
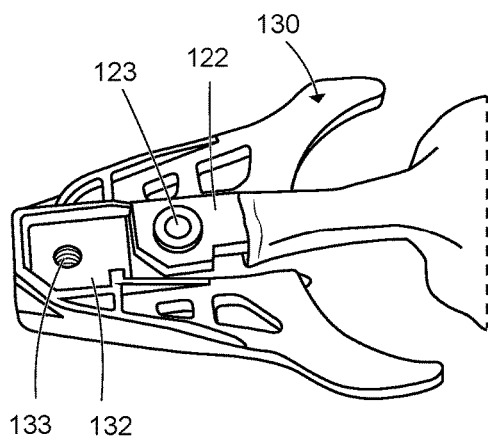
Figure 11D:
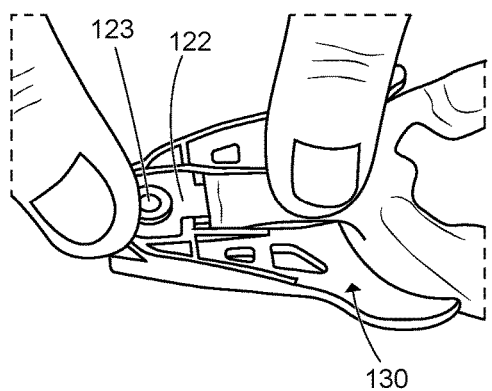
Figure 11E:
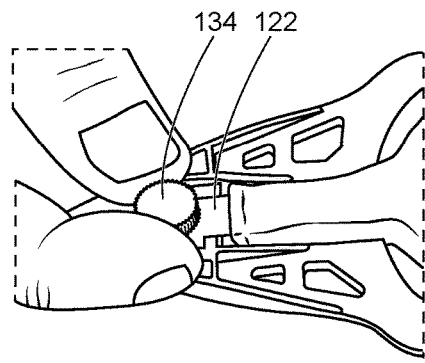
Figure 11F:
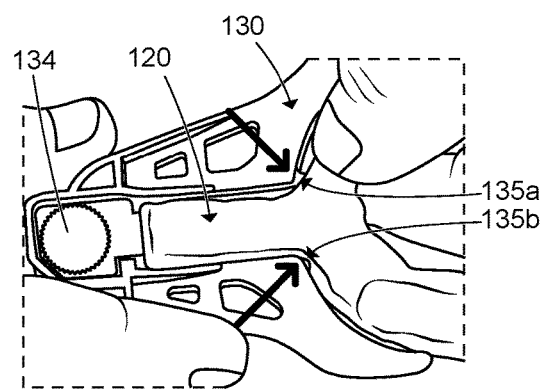
Figure 11G:
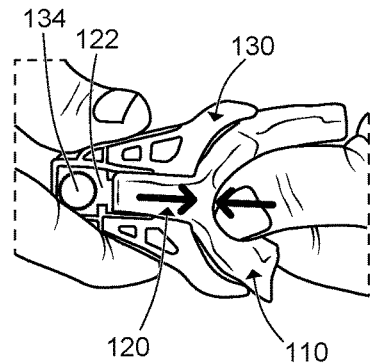
Figure 11H:
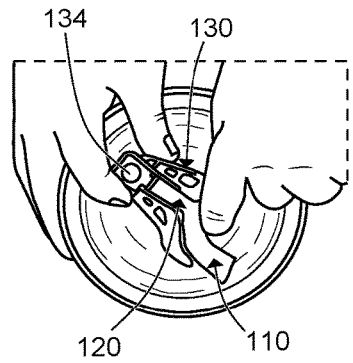
Figure 12A:
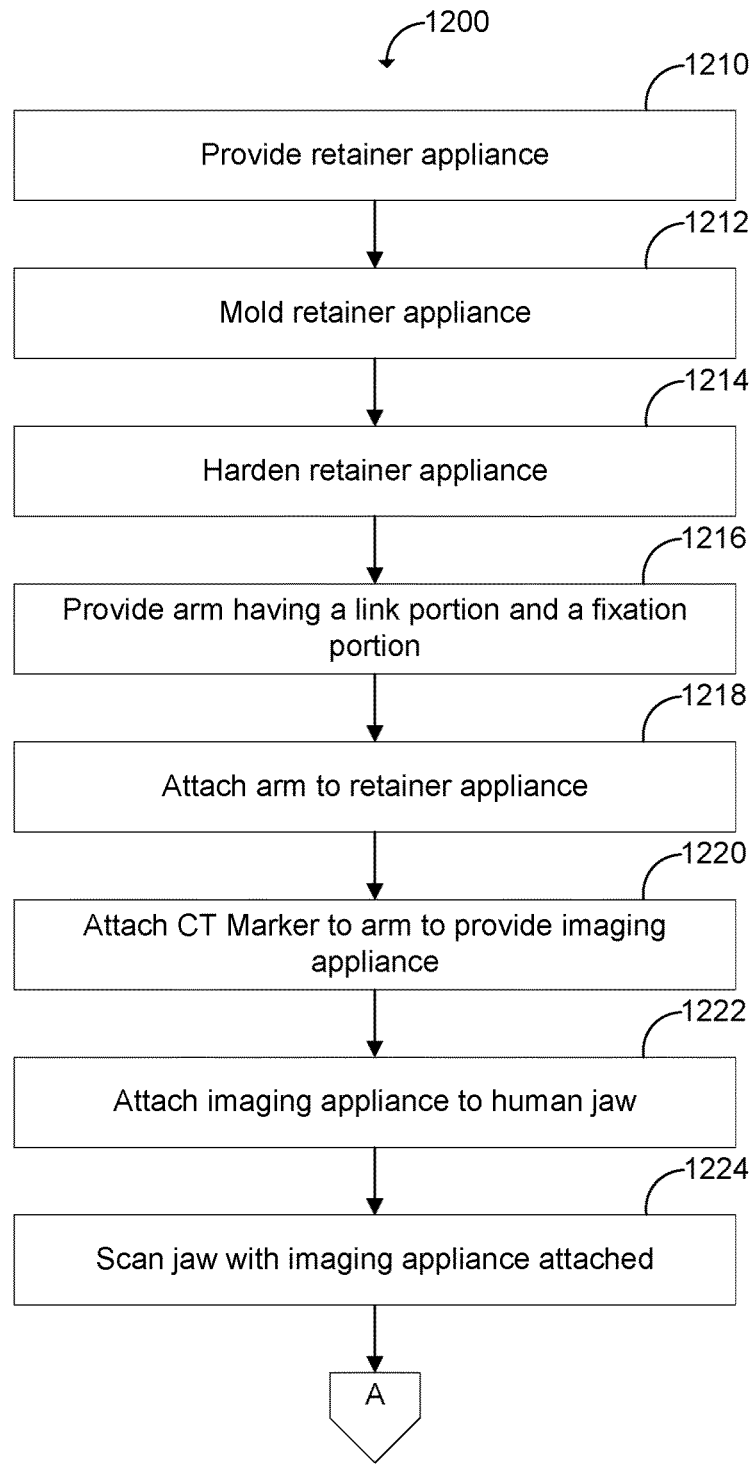
FIGS. 12A and 12B is a flowchart illustrating an example embodiment of a method for mapping a selected position on or within a human jaw to a volumetric CT image of the human jaw using the system of FIG. 8.
Figure 12B:
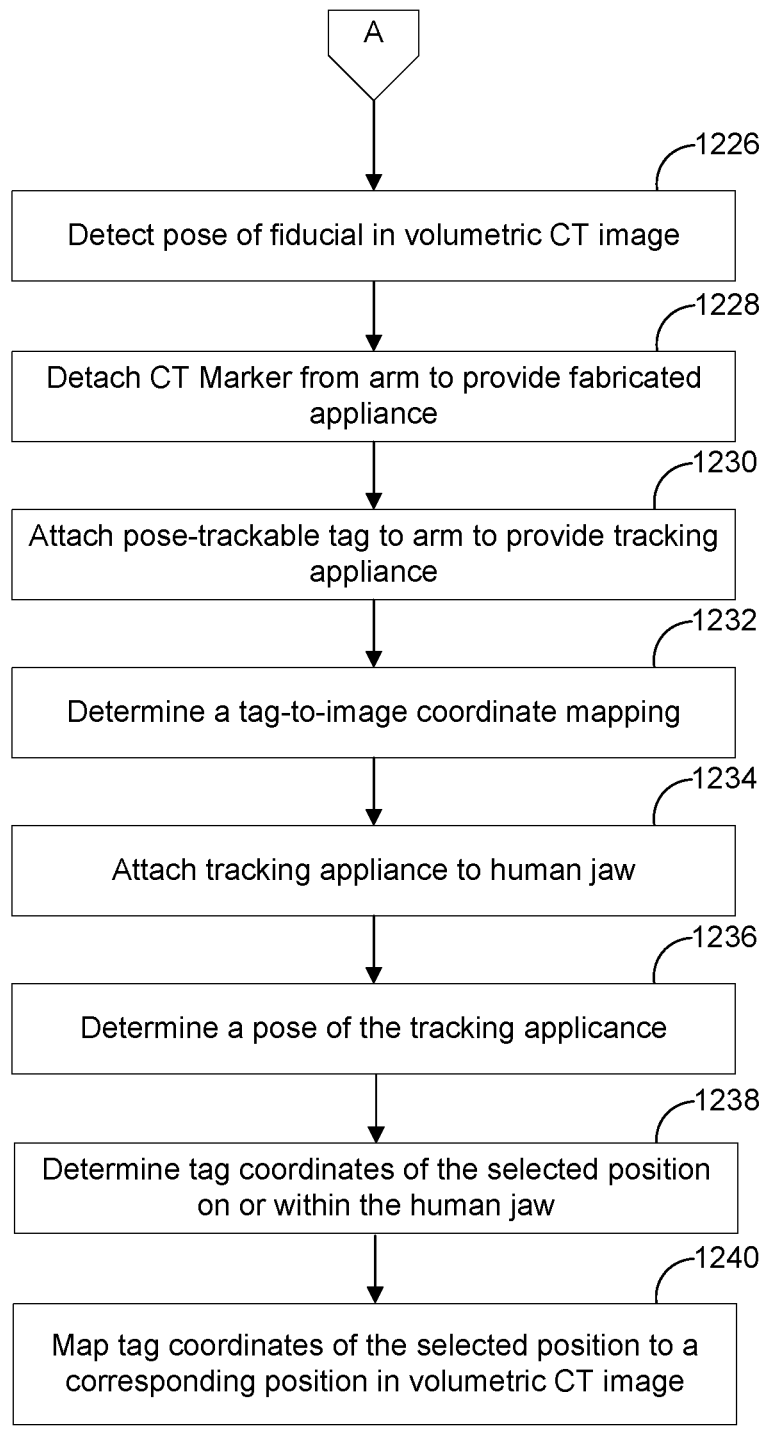

Referring now to FIG. 12, shown therein is an example method 1200 for mapping a selected position on or within a human jaw to a corresponding position in a volumetric CT image of that jaw. For example, the selected position on or within the human jaw may correspond to the tip of a surgical instrument being used in a surgical navigation procedure. This may allow a user to position and align the tip of the surgical instrument relative to the jaw, using the volumetric CT image of that jaw. The tip of the surgical instrument may also be positioned on or above an external surface of the jaw. To illustrate the method, reference will also be made to FIGS. 9 to 11, which show an example embodiment where the method 1200 is carried out on a facsimile 77 of a human jaw.

At 1210, a moldable retainer appliance can be provided. The retainer appliance can be moldable to an appliance geometry that mates with a surface geometry of at least a portion of a human jaw.

At 1212, the retainer appliance 10 can be pressed around the surface of the human jaw or a facsimile 77 thereof to shape the retainer appliance to conform to the surface geometry. Prior to pressing, the retainer appliance 10 may be softened and prepared for molding.

Figure 9A:
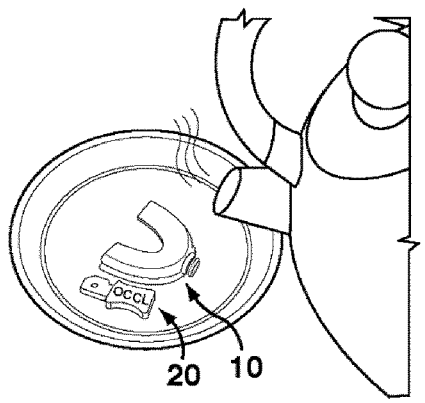
FIGS. 9A to 9F illustrate an example embodiment of a process for preparing a fabricated appliance for use in registering a human jaw with a volumetric CT image of the human jaw.

As shown in the example embodiment of FIG. 9A, the retainer appliance 10 and the link portion 21 can be immersed in hot or boiling water to heat them to a transition temperature for softening. In an example embodiment using Naviplast thermoplastic material (available from ClaroNav Inc., Toronto, Canada), immersion in boiling water may enable the retainer appliance 10 and link portion 21 to soften after 10 seconds. Once the retainer appliance 10 and link portion 21 have been heated, removal of the retainer appliance 10 and the arm 20 from the heat (i.e. hot water) is generally performed with care to not burn the user. In one example, gloves or utensils may be used to remove the retainer appliance 10 and the arm 20 from the hot water. Alternatively, the hot water may be poured out.

Figure 9B:
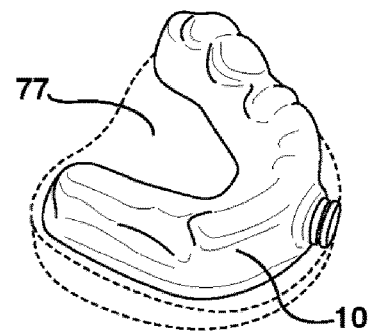

As shown in FIG. 9B, the retainer appliance 10 can be inserted into a patient's mouth and pressed around the surface of the human jaw or pressed around a facsimile 77 to shape the retainer appliance 10. As mentioned above, the retainer appliance 10 may be manufactured from a moldable material having low thermal conductivity so that the retainer appliance 10 will not burn the patient's mouth after being heated to the transition temperature.

By pressing the retainer appliance 10 around the human jaw or a facsimile 77, the retainer appliance 10 may conform to the surface geometry of the human jaw 77. Vertical wall region 15 of the retainer sheet 11 may generally be aligned with the buccal cusps first, followed by pressing of the top surface region 16 against the underlying lingual surface of the teeth and gums to form a tight contact.

The retainer appliance 10 may then be hardened at 1214. The retainer appliance 10 can be hardened so as to retain the appliance geometry and resist deformation. In some embodiments, the retainer appliance 10 may be cooled down and hardened by leaving it in the patient's mouth for a minute. As mentioned above, in various embodiments the retainer appliance 10 (and link portion 21) can be manufactured from a material with low or no shape memory so that it retains its molded form once hardened.

At 1216, an arm can be provided that includes a moldable link portion and a rigid fixation portion. The various embodiments of arms described herein may be used at 1216. The arm 20 may be provided prior to molding the retainer appliance 10. In some cases, the link portion 21 can be simultaneously softened, e.g. where the arm 20 is mounted to the retainer appliance 10 while the retainer appliance 10 is being molded to the human jaw. This may allow the link portion 21 to be substantially simultaneously molded to provide the desired support position for the fixation portion 22.

Figure 9C:
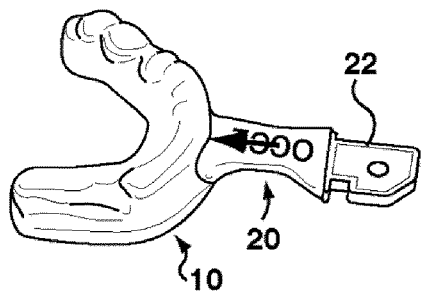

At 1218, the arm 20 may be rigidly attached to the retainer appliance 10. The link portion 21 of the arm 20 may be rigidly attached to the retainer appliance 10 to hold the fixation portion 22 in a fixed support position with respect to the retainer appliance 10. For example, the link portion 21 may be mounted onto the retainer appliance 10 at the rigid retainer connector 12 disposed along the spine 14 of the retainer sheet 11, as shown in FIG. 9C. Similarly, FIGS. 11A and 11B show arm 120 having a base and being mounted to the retainer appliance 110. As described above, denture adhesive may be added between the base and the retainer appliance 110 to secure the connection.

At 1220, the CT marker 30 can be detachably attached to the fixation portion 22 at a CT marker connection region to provide an imaging appliance. In some embodiments, the CT marker 30 can be detachably attached to the fabricated appliance to provide an imaging appliance prior to attaching the imaging appliance to the human jaw. In some cases, the CT marker 30 may be detachably attached to the fixation portion 22 while the link portion 21 is being molded to ensure that the support position allows the CT marker 30 to be captured in a scanned image of the human jaw.

As shown in FIG. 10C, the CT marker 30 may be connected to the fabricated appliance by mating the rigid fixation portion 22 with the connector 32. The CT marker 30 can be maintained in a fixed spatial relationship with the arm 20 and thus the fabricated appliance while attached thereto. In some cases, the connection can be further secured by aligning bores 23 and 33, and inserting and tightening a screw 34 through the bores 23 and 33.

Figure 9D:
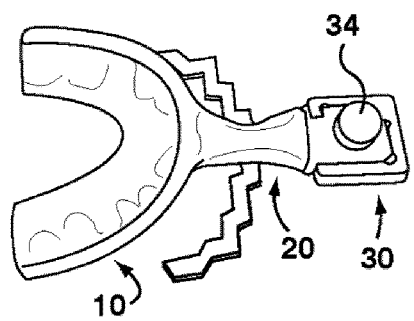

In some cases, the CT marker 30 may be attached to the rigid fixation portion 22 after the arm 20 is mounted to the retainer appliance 10 to provide an imaging appliance, as shown in FIG. 9D. The CT marker 130 may be connected to the arm 120 by mating the rigid fixation portion 122 with the fiducial connector 132, as shown in FIGS. 11C and 11D. In some cases, the connection may further include aligning bores 123 and 133, and inserting and tightening a screw 134 through bores 123 and 133, as shown in FIG. 11E.

Figure 9E:
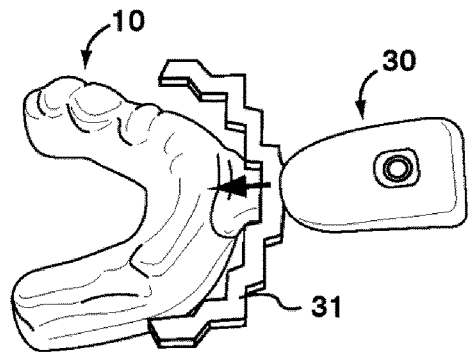

As shown in FIG. 9E, in some cases the CT marker 30 can be detachably attached to the rigid fixation portion 22 prior to molding and hardening the moldable link portion 21. The arm 20 and CT marker 30 can be pushed towards the retainer appliance 10 to mold the moldable link portion 21. When the CT marker 30 is in the desired position with respect to the retainer appliance 10, the moldable link portion 21 can then be hardened to rigidly secure the fixation portion 22 in the support position.

As explained above, molding the link portion 21 can include heating the moldable link portion 21 to the transition temperature prior to pushing the CT marker 30. By pushing, the support position, and thus the position of the CT marker 30 attached to the rigid fixation portion 22 can be adjusted to ensure that at least some of the distinct features of the fiducial will appear in a scanned image of the human jaw. This can provide greater accuracy and reliability in the registration. As shown in FIGS. 11F and 11G, the CT marker 130 may also be pushed toward the retainer appliance 110 so that the link engaging members 135a and 135b engage with the base of the link portion 121 as explained above.

In some cases, the retainer appliance 10 may be hardened prior to mounting 1216 the arm 20 and hardening the moldable link portion 21. In other cases, the retainer appliance 10 and the moldable link portion 21 can be hardened substantially concurrently.

In an example embodiment, the retainer appliance 10 and the moldable link portion 21 can be removed from the human jaw for cooling and immersed in cold water for approximately 30 seconds. In some embodiments, the retainer appliance 110 and the moldable link portion 121 may be hardened with the CT marker 130 connected thereto, as shown in FIG. 11H. Once the retainer appliance 10 has been hardened and the arm 20 has been mounted to the retainer appliance 10, the fabricated appliance has been formed.

Figure 9F:
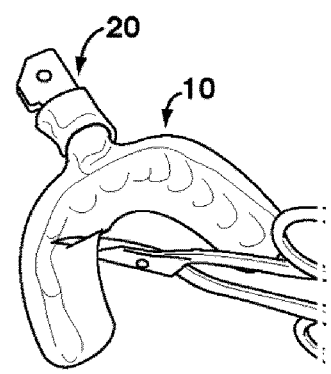

In some cases, segments of the fabricated appliance may be removed to uncover regions where access to the human jaw is required for surgery. As shown in FIG. 9F, segments of the fabricated appliance may be removed using scissors without the CT marker 30 connected. In this example embodiment, scissors having short blades of less than 10 millimeters may easily cut the fabricated appliance at various angles. Other utensils may also be used to cut the fabricated appliance, including but not limited to blades, hole-punches, and laser cutters.

In alternative embodiments, although the CT marker 30 may impede manipulation of the fabricated appliance, segments of the fabricated appliance may be removed while the CT marker 30 remains connected to the arm 20. FIGS. 4C, 6A, and 10A show fabricated appliances with segments removed. The segments removed may indicate missing teeth, where dental implants may be inserted during surgery.

At 1222, the imaging appliance may be attached to the human jaw. FIG. 10C shows an example embodiment of the imaging appliance attached to the human jaw.

At 1224, the human jaw may be scanned with the imaging appliance attached thereto. The scan can be used to obtain a volumetric CT image of at least a portion of the fiducial and a portion of the human jaw in the volumetric CT image.

At 1226, the pose of the fiducial can be detected in the volumetric CT image using a data processor 804. The pose of the fiducial can be used to derive a fiducial-to-image coordinate mapping. The fiducial-to-image coordinate mapping can then be stored in the database memory 806.

The fiducial-to-image coordinate mapping can be derived by operating a data processor 804 to map the coordinate space (e.g. six degrees of freedom) of a reference fiducial to the coordinate space (e.g. six degrees of freedom) of the three-dimensional volume image. The data processor 804 can be operated to obtain a three-dimensional mapping transformation from the reference image to the scanned volume image based on the at least three distinct features of the fiducial 31 in the scanned image. The data processor 804 may do this by first aligning the fiducial 31 in the three-dimensional volume image to be congruent with a reference fiducial model. In some cases, this alignment can be performed based on the identified distinct features.

After scanning, at 1228 the imaging appliance may be removed from the human jaw and the CT marker 30 may be detached from the imaging appliance to provide the fabricated appliance again.

Subsequently, at 1230 a pose-trackable tag 80 may be detachably attached to the fixation portion at a tag connection region to provide the tracking appliance. A configuration of the tag connection region of the fixation portion relative to the CT marker connection region of the fixation portion may have a fixed tag-to-fiducial coordinate mapping prior to attaching any one of the tag and the CT marker. The tag 80 may be detachably attached to the fabricated appliance in the same manner as the CT marker 30.

At 1232, the previously stored tag-to-fiducial coordinate mapping and the fiducial-to-image coordinate mapping determined at 1226 can be used to determine a tag-to-image coordinate mapping.

At 1234, the tracking appliance can then be attached to the human jaw. The tracking appliance may be attached to the human jaw for use in surgical navigation. FIG. 10D shows an example of a tracking appliance attached to the human jaw.

At 1236, the pose of the tracking appliance can be determined using a pose measurement system. As mentioned above, the pose measurement system may measure or track portions of the tag that are optically, or electromagnetically, or otherwise detectable to determine the pose.

At 1238, with the tracking appliance attached to the human jaw, the human jaw can be tracked using the tag of the tracking appliance. Tag coordinates of the portion of the human jaw in a coordinate system of the tag can be determined using the pose of the tracking appliance.

At 1240, the tag coordinates of the selected position on or near the human jaw can be mapped to a corresponding position in the volumetric CT image. This may be done by combining the tag-to-image coordinate mapping determined at 1232, with the determined pose of the tag.

The tag 80 may be automatically mapped to the coordinate space of the three-dimensional scanned image without additional steps to determine the geometrical relationship between the tag 80 and the fabricated appliance. This mapping transformation may be pre-defined because the rigid fixation portion 22 is used to detachably attach to both the connector 32 and the tag connector 82. As set out above, the detachable connection provided by the rigid fixation portion 22 allows the spatial relationship between the position of the CT marker 30 on the fabricated appliance and the position of the tag assembly 80 on the fabricated appliance to be known and fixed in advance, and stored.

Given that the geometrical relationship between the rigid fixation portion 22 and the connector 32 and the tag connector 82 respectively can be pre-determined, this can allow the tag assembly 80 and CT marker 30 to be used with a plurality of different fabricated appliances, e.g. for appliances fabricated for different patients. The geometrical relationship between the CT marker 30 and the tag assembly 80 can be independent of the particular fabricated appliance and stored for use in tracking during surgery.

Once the coordinate space of the reference fiducial is mapped to the coordinate space of the three-dimensional scanned image, a navigation mapping between the human jaw and the human jaw in the scanned image may be automatically determined. A data processor may be operated to use this navigation mapping to implement various pose tracking methods, such as those described in PCT Application No. PCT/CA2011/001294. The pose tracking methods may map locations in the interior of the human jaw to corresponding locations in the three dimensional volume representation of the interior region.

The fabrication method described herein may be used for the fabrication of an appliance for a human jaw. In various embodiments, the jaw may be either a lower jaw (mandible) or an upper jaw (maxilla), and may have any pattern of partial edentulism. Scanners such as CT scanners and other image data may also provide information regarding the orientation of the patient's head relative to the image coordinates. By combining the orientation of the patient's head relative to the image coordinates, along with information about the direction of occlusion, the human jaw may be identified as either a maxilla or a mandible.

Various embodiments have been described herein by way of example only. Various modification and variations may be made to these example embodiments without departing from the spirit and scope of the invention, which is limited only by the appended claims.

The invention claimed is:

1. A method for mapping a selected position on or within a human jaw to a corresponding position in a volumetric CT (computerized X-ray tomography) image of that jaw, the method comprising:
    providing a moldable retainer appliance;
    molding the retainer appliance to have an appliance geometry that mates with a surface geometry of at least a portion of the human jaw, such that when mated to the human jaw, the retainer appliance resists displacement relative to the human jaw;
    hardening the appliance to retain the appliance geometry and resist deformation;
    providing an arm comprising a moldable link portion and a rigid fixation portion;
    rigidly attaching the link portion to the retainer appliance to maintain a fixed spatial mapping between the fixation portion and the retainer appliance to provide a fabricated appliance;
    detachably and rigidly attaching a CT marker including a fiducial detectable in the volumetric CT image to the fixation portion at a CT marker connection region to provide an imaging appliance including the fabricated appliance and the CT marker;
    attaching the imaging appliance to the human jaw;
    scanning the human jaw with the imaging appliance attached thereto to obtain the volumetric CT image of at least a portion of the fiducial and a portion of the human jaw in the volumetric CT image;
    detecting the pose of the fiducial in the volumetric CT image to derive a fiducial-to-image coordinate mapping;
    detaching the CT marker from the fixation portion to provide the fabricated appliance;
    detachably and rigidly attaching a pose-trackable tag to the fixation portion at a tag connection region to provide a tracking appliance including the fabricated appliance and the tag, wherein a configuration of the tag connection region relative to the CT marker connection region ensures a fixed tag-to-fiducial coordinate mapping prior to attaching any one of the tag and the CT marker;
    determining a tag-to-image coordinate mapping using the tag-to-fiducial coordinate mapping and the fiducial-to-image coordinate mapping;
    attaching the tracking appliance to the human jaw;
    determining a pose of the tracking appliance using a pose measurement system;
    determining tag coordinates of the selected position in a coordinate system of the tag using the pose of the tracking appliance; and
    mapping the tag coordinates of the selected position to a corresponding position in the volumetric CT image using the tag-to-image coordinate mapping.

2. The method according to claim 1, wherein:
the link portion is rigidly attached to the appliance by:
heating the link portion to a link transition temperature such that the link portion becomes soft and malleable;
placing the link portion into contact with the retainer appliance;
securing the link portion to the retainer appliance; and
hardening the link portion to remain rigid and resist deformation such that the link portion is rigidly attached to the appliance and maintains the fixed spatial mapping between the fixation portion and the retainer appliance.

3. The method according to claim 2, further comprising:
detachably and rigidly attaching the CT marker to the fixation portion at the CT marker connection region prior to attaching the link portion to the retainer appliance;
placing the link portion into contact with the retainer appliance and securing the link portion to the retainer appliance by
rigidly fixing an end of the softened link portion to the retainer appliance;
pushing the arm, with the CT marker attached thereto, in a direction towards the appliance such that the softened link portion is molded to allow the fixation portion to be fixed in a support position relative to the retainer appliance such that at least a portion of the fiducial will appear in the volumetric CT image of the human jaw when the imaging appliance is attached to that jaw; and
hardening the link portion such that the link portion is rigidly attached to the appliance with the fixation portion in the support position.

4. The method according to claim 3, wherein securing the link portion to the retainer appliance comprises gluing the link portion to the retainer appliance.

5. The method according to claim 4, wherein molding the retainer appliance to have the appliance geometry comprises:
heating the retainer appliance to a retainer transition temperature such that the retainer appliance becomes soft and malleable; and
pushing the softened retainer appliance into contact with the at least a portion of the human jaw having the surface geometry.

6. The method according to claim 5, further comprising:
heating the link portion to a link transition temperature such that the link portion becomes soft and malleable;
detachably and rigidly attaching the CT marker to the fixation portion at the CT marker connection region, the CT marker having at least one link engaging member;
molding the link portion by pushing the at least one link engaging member into a surface of the link portion so that the at least one link engaging member deforms the surface of the link portion to provide at least one indentation corresponding to the at least one link engaging member; and
hardening the link portion such that, when the CT marker is detachably attached to the fixation portion at the CT marker connection region, each link engaging member is receivable within the corresponding indentation and the CT marker is thereby restrained from moving relative to the link portion.

* * * * *